Figure 1:
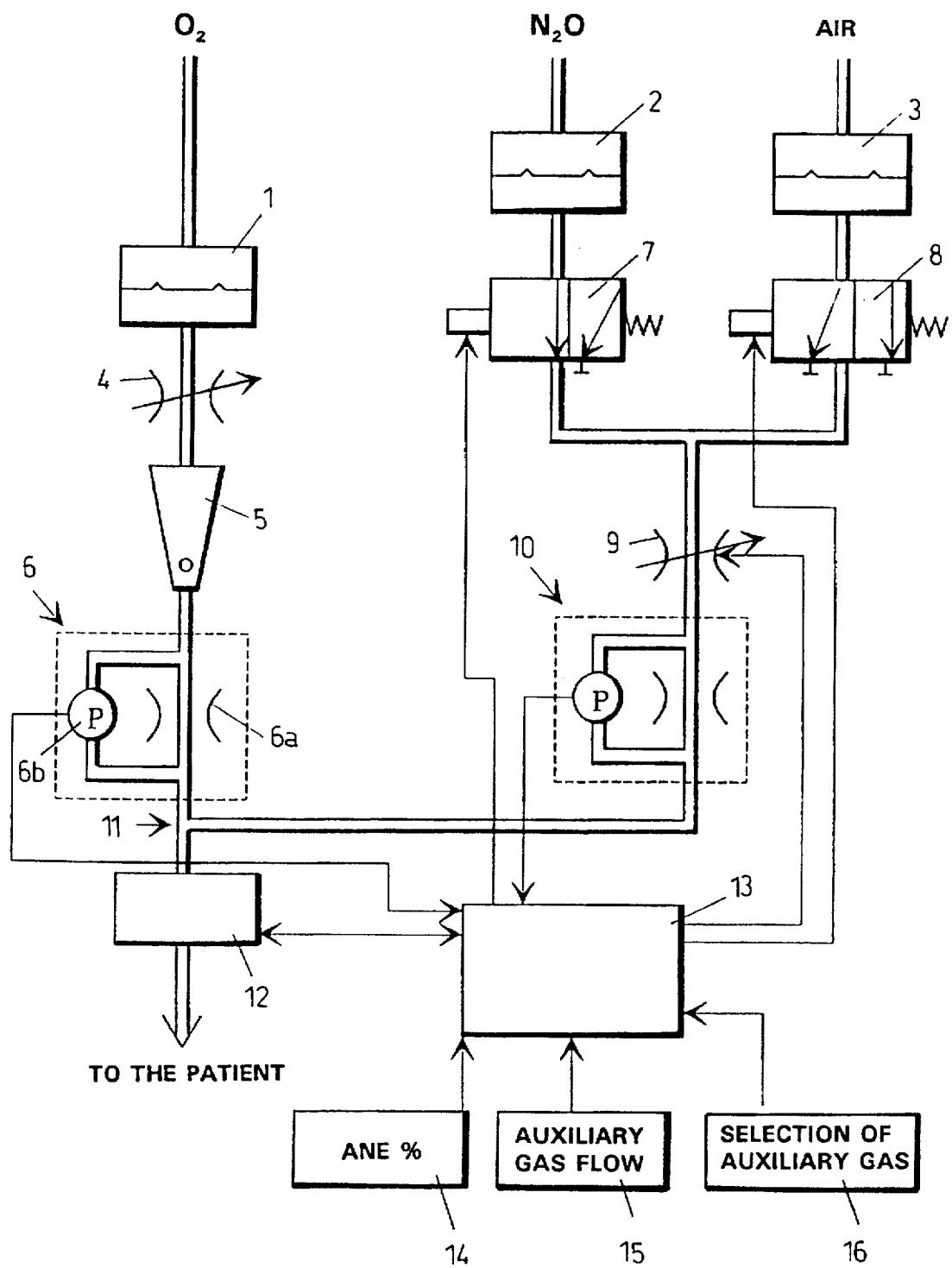

United States Patent
Heinonen et al.

[11] Patent Number: 5,722,449
[45] Date of Patent: Mar. 3, 1998

[54] ARRANGEMENT IN CONNECTION WITH A GAS MIXER

[75] Inventors: Erkki Heinonen; Markku Paloheimo, both of Helsinki, Finland

[73] Assignee: Instrumentarium Oy, Helsinki, Finland

[21] Appl. No.: 868,469

[22] Filed: Jun. 3, 1997

Related U.S. Application Data

[63] Continuation of Ser. No. 432,057, May 1, 1995, abandoned.

[30] Foreign Application Priority Data

May 6, 1994 [FI] Finland .................... 942119

[51] Int. Cl.[6] .................... A61M 16/10; G05D 11/13
[52] U.S. Cl. .................... 137/101.19; 128/203.25; 128/204.21; 137/101.21
[58] Field of Search ............ 137/88, 101.19, 137/101.21, 607; 128/203.25, 204.21

[56] References Cited

U.S. PATENT DOCUMENTS

| | | | |
|---|---|---|---|
| 4,237,925 | 12/1980 | Urushida | 137/607 X |
| 4,328,823 | 5/1982 | Schreiber | 137/88 |
| 4,345,612 | 8/1982 | Koni et al. | 137/101.19 |
| 4,526,188 | 7/1985 | Olsson et al. | 137/88 X |
| 4,576,159 | 3/1986 | Hahn et al. | 128/203.25 X |
| 5,205,322 | 4/1993 | Merick et al. | 137/88 X |
| 5,435,332 | 7/1995 | Heinonen | 137/607 |

FOREIGN PATENT DOCUMENTS

| | | |
|---|---|---|
| 98193 | 1/1984 | European Pat. Off. |
| 361134 | 4/1990 | European Pat. Off. |
| 361134 | 10/1990 | European Pat. Off. |
| 343542 | 12/1992 | European Pat. Off. |
| 92468 | 8/1994 | Finland |
| 2548549 | 1/1985 | France |
| 2136703 | 9/1984 | United Kingdom |
| 2240849 | 8/1991 | United Kingdom |
| 2254258 | 10/1992 | United Kingdom |

*Primary Examiner*—Stephen M. Hepperle
*Attorney, Agent, or Firm*—Andrus, Sceales, Starke & Sawall

[57] ABSTRACT

An arrangement in connection with a gas mixer, which is arranged to form a mixed gas of oxygen and another gas to be mixed with it. To provide a simple and reliable arrangement, before the mixed gas is formed the oxygen is arranged to be supplied through both a mechanical adjusting means, and a mechanical and electronic flow-measuring means. The other gas to be mixed with oxygen is arranged to flow through an electronic flow-measuring device. The flow of the other gas is arranged to be regulated by means of an electronically controlled regulating valve, whereupon the electronic flow-measuring means, the electronic flow-measuring device, and the electronically controlled regulating valve are arranged to be operated by means of a control unit.

18 Claims, 4 Drawing Sheets

5,722,449

1

ARRANGEMENT IN CONNECTION WITH A GAS MIXER

CROSS REFERENCE TO RELATED APPLICATIONS

The present application is a continuation of U.S. patent application, appln. Ser. No. 08/432,057, filed May 1, 1995, and now abandoned.

The invention relates to an arrangement in connection with a gas mixer, which is arranged to form a mixed gas of oxygen and another gas to be mixed with it.

In the field, a gas mixer refers to a device in which a mixed gas is formed of oxygen and an anaesthetic gas, or of a mixture of oxygen, an anaesthetic gas and air, and the mixed gas can be passed, for example, to a vaporized anaesthetic agent and be mixed with it. The anaesthetic agent can be vaporized in a vaporizer of which several different types are known.

The anaesthetic gas is normally $N_2O$. However, the aforementioned normal anaesthetic gas may also be replaced in the mixture with normal air. The gas mixture consisting of oxygen, an anaesthetic gas and a possibly vaporized anaesthetic agent is supplied to a patient circuit, and in the field of anaesthesia this gas mixture is generally called a fresh gas.

The minimum oxygen concentration of the fresh gas required by the standards of the field is 21%, but in practice the permitted minimum is typically about 23 to 25%, and on the other hand, concentrations as low as 25 to 27% are preferred in the gas mixture. To ensure this, devices have been built in the gas mixers to guarantee the oxygen concentration of the gas in cases of failures in the oxygen supply pressure, and breakdowns in the operation.

The effect of operational breakdowns is eliminated by means of the mechanical couplings of control valves situated in the flow conduits of oxygen and anaesthetic gas. One example of such arrangements is disclosed in GB Patent 2,136,703. The disadvantage of this arrangement is that it does not eliminate the decrease of the oxygen concentration caused by the dropping of the oxygen supply pressure. In order to eliminate this, a separate means controlling the pressures is needed, this means interrupting the flow of the anaesthetic gas if the pressure of oxygen decreases. Furthermore, due to the small range of variation permitted for the minimum oxygen concentration, the valves and the couplings between the valves are required to comprise fine mechanics.

Another example of the prior art is a pneumatic restrictor, which is disclosed for example in U.S. Pat. No. 4,328,823. In this arrangement, both the oxygen and anaesthetic gas line comprise a pressure chamber proportionate to the amount of gas flowing in the conduit, and the anaesthetic gas conduit also comprises a separate flow restrictor. The pressures of the chambers are compared with each other, and the result of the comparison is supplied to the flow restrictor of the anaesthetic gas conduit. Thus, if the flow of oxygen is too small compared to the flow of the anaesthetic gas, resulting in too low an oxygen concentration in the mixture, the pressure in the pressure chamber coupled to the oxygen conduit falls, and the comparison to the pressure chamber of the anaesthetic gas conduit makes the flow restrictor of the anaesthetic gas act in such a way that the balance between the pressure chambers is maintained. The disadvantages of the arrangement include delicate moveable parts, and a flexible rubber diaphragm which compares the pressure between the pressure chambers and which has to be replaced at regular intervals. Furthermore, the pressures created in the flow conduits by the more common small flows are very low, and thus the operation of the device is not reliable. Therefore the restrictors require either a certain minimum oxygen flow or a separate coupling by mean of which the entire device can be bypassed when the flow is less than 1 l/min.

A new disadvantage of the prior art arrangements, which has occurred only recently, relates to the novel anaesthetic, desflurane. The concentration of the conventional anaesthetics in the fresh gas is at most 5%. However, with desflurane it may be 18%. Thus, if the concentration of the mixture of oxygen and anaesthetic gas is 25%, the concentration of the fresh gas is already less than 21%. To maintain the concentration above 21%, the minimum concentration of the restrictor has to be set higher, which in turn results in too high a minimum oxygen concentration when conventional anaesthetics are used. In a pneumatic restrictor disclosed for example in GB Patent 2,254,258, this is realized by means of a separate stepwise selecting unit which is coupled to the concentration regulator of the vaporizer.

Both types of device described above also comprise an unsolved problem relating to the vaporization of the anaesthetic agent into the air. No mechanism restricting the concentration is installed in the air conduit, wherefore dosing is possible even without an oxygen flow. If vapour formed of the anaesthetic agent is administered into clean air, this immediately results in a lower oxygen concentration of the fresh gas than what is permitted. The problem is especially severe in the use of desflurane when the oxygen concentration may be 17%.

Both of the above-described arrangements are based on mechanical action. Designs have been presented for arrangements which control the distribution of oxygen and anaesthetic gas completely electronically by using electronic flow measurement and electronically controlled flow regulating valves. To safeguard the vital functions of the patient under all circumstances, continuous supply of oxygen is of crucial importance. This cannot be achieved with electronic arrangements.

The purpose of the invention is to provide an arrangement by means of which the drawbacks of the prior art can be eliminated. This is achieved with the arrangement according to the invention, which is characterized in that before the mixed gas is formed, the oxygen is arranged to be supplied through both a mechanical adjusting means, and a mechanical and electronic flow-measuring means, that the other gas to be mixed with oxygen is arranged to flow through an electronic flow-measuring device, and that the flow of the other gas is arranged to be regulated by means of an electronically controlled regulating valve, whereupon the electronic flow-measuring means, the electronic flow-measuring device, and the electronically controlled regulating valve are arranged to be operated by means of a control unit.

The most important advantages of the arrangement according to the invention are its simplicity and the reliability of its operation. The reliability results for example from the fact that the distribution of oxygen is completely independent of the supply of electricity and of possible malfunctions occurring in the electronic device. A further advantage of the invention is its versatility, since in the administering of the anaesthetic gas the electronic control mechanism and the new electronically controlled flow regulating elements provide a number of possibilities of solving the aforementioned problems. The set value of the anaesthetic gas flow can be electronically adjusted advantageously. The regulating element of the anaesthetic gas flow is controlled by means of software in such a way that the prevailing mechanically set oxygen flow and the selected anaesthetic agent concentration together with the anaesthetic gas flow do not cause too low an oxygen concentration of the fresh gas. The use of air to replace the anaesthetic gas does not cause any problems either, since the electronically controlled vaporizer may be closed automatically if the oxygen concentration of the gas mixture drops too low. The arrangement according to the invention automatically cuts off at least the anaesthetic gas flow if malfunctions or interruptions occur in the electricity supply system of the control unit, and the anaesthesia can be completed safely by means of pure oxygen and a mechanical flow meter. When the oxygen supply pressure stops, the oxygen flow also diminishes, and if as a result of this the oxygen concentration of the fresh gas drops too low, the anaesthetic gas flow is decreased, and when the oxygen runs out completely, the anaesthetic gas flow also stops.

Figure 2:
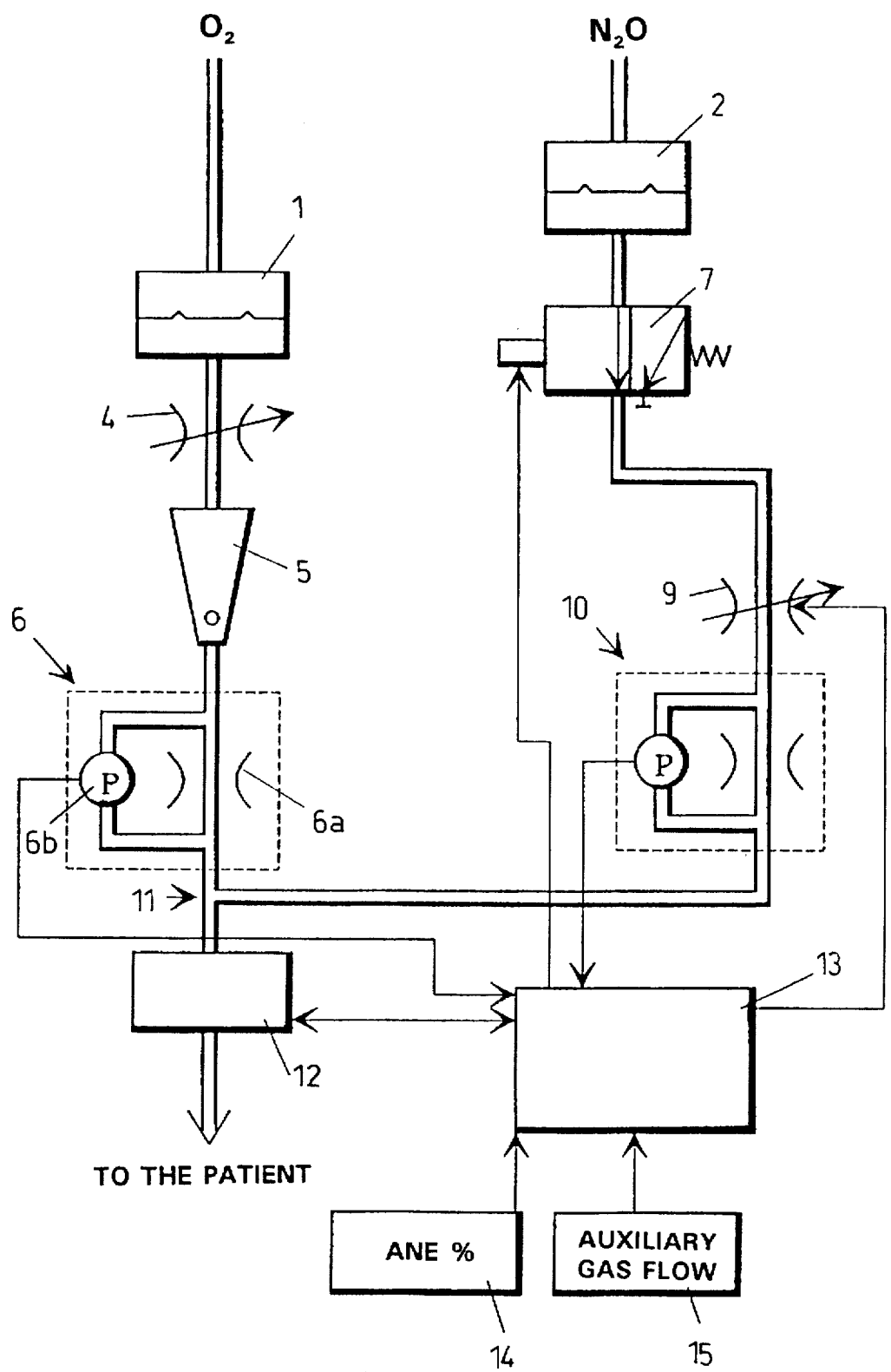
Figure 3:
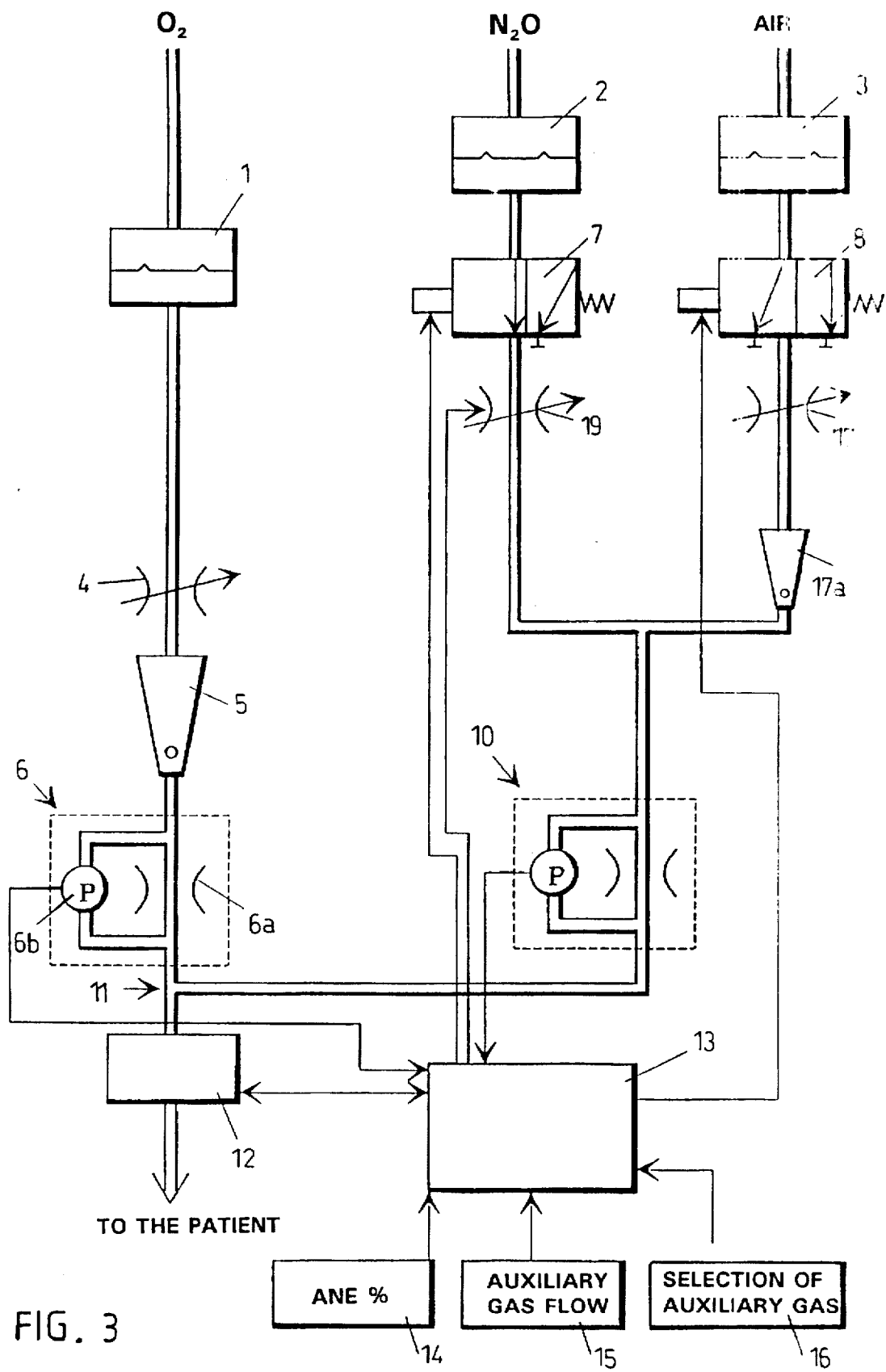
Figure 4:
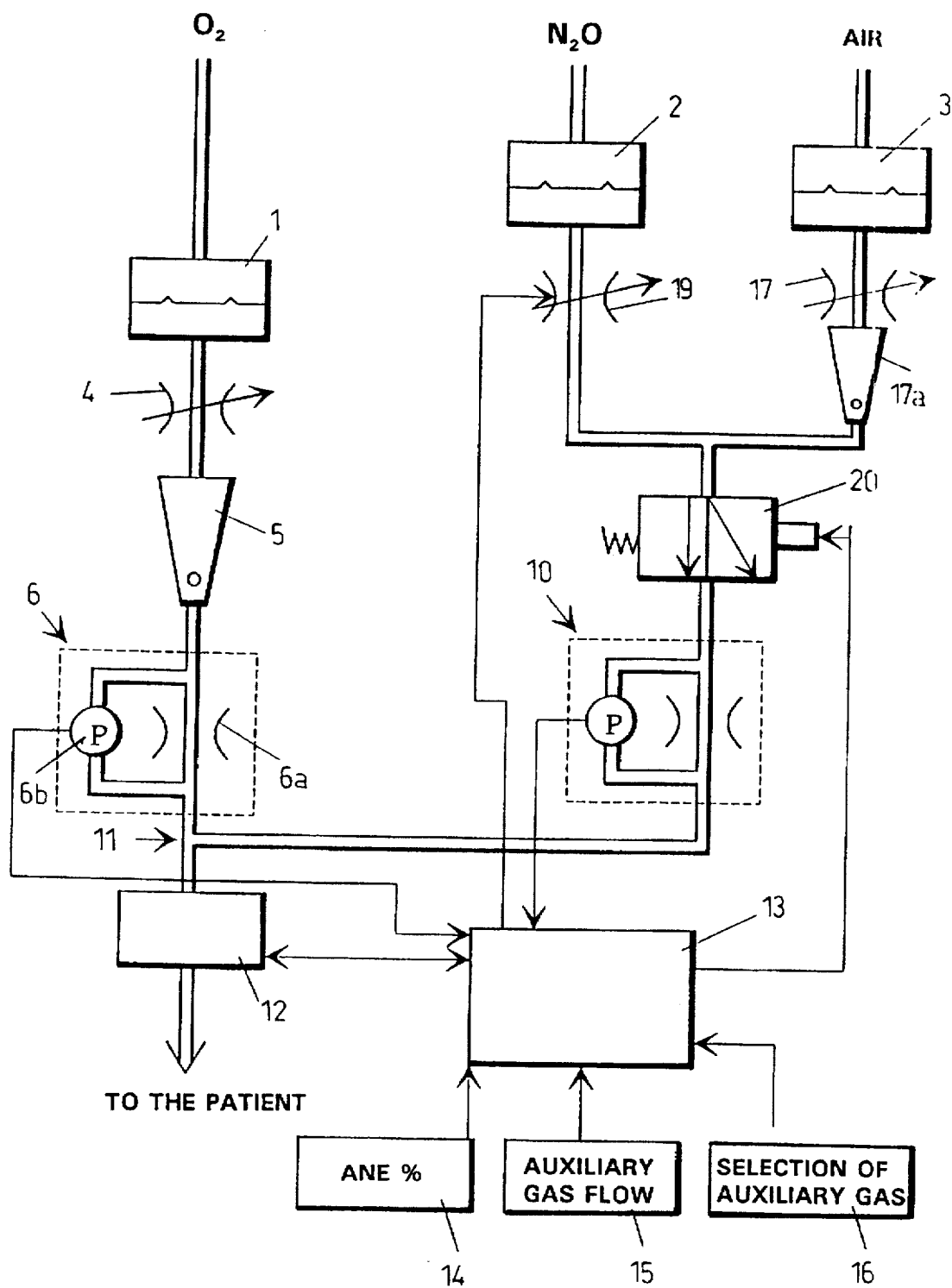

In the following, the invention will be described in greater detail by means of embodiments shown in the accompanying drawing, in which FIG. 1 is a schematic diagram of a first embodiment of the arrangement according to the invention, FIG. 2 is a schematic diagram of a modification of the arrangement of FIG. 1, FIG. 3 is a schematic diagram of a second embodiment of the arrangement according to the invention, and FIG. 4 is a schematic diagram of a third embodiment of the arrangement according to the invention.

FIG. 1 shows schematically the first embodiment of the arrangement according to the invention. In the example of FIG. 1, the pressure supplies of oxygen and another gas, in this case anaesthetic gas and air, are conveyed to pressure regulators, which are denoted by reference numerals 1, 2 and 3. The oxygen is passed further, after a pressure regulator 1 situated in the oxygen line, through a mechanical adjusting means 4, and a mechanical and electronic flow-measuring means 5, 6. The means 6 may be for example a mass flow meter, or as in the example of FIG. 1, a meter based on a throttle 6a and on the pressure difference created by the throttle and measured by means of a pressure sensor 6b. The mechanical and electronic flow-measuring means 5, 6 may be formed into separate devices as in FIG. 1. However, it is also quite possible to form an arrangement where the aforementioned mechanical and electronic flow measurement is performed by means of one and the same device. Neither is it necessary to place the pressure regulators in the same way as in FIG. 1, but the devices used in the regulation of the pressure can be placed, if necessary, also outside the gas mixer, etc.

In the anaesthetic gas line, i.e. the $N_2O$ line, and in the air line there are electronically controlled on/off-type means 7, 8 which regulate the flow. The other gas to be mixed with oxygen is selected with the means 7, 8. The means 7 is normally a closed valve, i.e. it is opened as a result of electric activation and it closes automatically when the electric activation ends. The means 8 is in turn arranged to close as a result of electric activation and to open after the electric activation ends. The flow of the gas selected with the means 7, 8 is regulated with an electronically controlled flow regulating valve 9. The means 7, 8 also act as a safety mechanism for the valve 9. If there is something wrong with the valve 9 so that it cannot be closed, the flow can be interrupted advantageously also with the means 7, 8.

The flow of the other gas to be mixed with oxygen is measured by means of an electronic flow-measuring device 10, which is preferably similar to the electronic flow-measuring means 6 situated in the oxygen line. The electronic flow-measuring device may be placed in the arrangement in such a way that the other gas flows through it before it is mixed with oxygen. FIG. 1 shows such an embodiment. However, the electronic flow-measuring device may also be placed in such a way that it is situated in the arrangement downstream of the mixing point. In such an embodiment, the mixture formed by the other gas and oxygen flows through the electronic flow-measuring device. The amount of the other gas may thus be calculated from the measuring information obtained from the electronic flow-measuring device. The gas mixture forming at point 11 in the conduit is passed in this example to a vaporizer 12. The vaporizer 12 may be of any type known in the field. The structure and operation of the vaporizer constitute fully conventional technology to one skilled in the art, wherefore they are not described in greater detail in this connection. From the vaporizer 12, the mixture may be delivered to the patient in a conventional manner. It is clear that the structure depends on the type of the vaporizer used, i.e. the gas mixture is not naturally passed to the vaporizer if such a vaporizer is used where the mixing takes place for example outside the vaporizer. Due to the structure of the vaporizer, the vaporization may take place either in the vaporizer or from the vaporizer.

In the example of FIG. 1, the vaporizer is preferably an electronically controlled device, so that a control unit 13 knows the predetermined anaesthetic agent concentration of the fresh gas. The set value of the oxygen flow is adjusted by means of the valve 4, and the set values of the anaesthetic agent concentration of the fresh gas, the gas to be mixed with oxygen, and the flow of the gas to be mixed with oxygen are adjusted by means of the electronic devices 14, 15, 16. The electronic flow-measuring means 6, the electronic flow-measuring device 10, and the electronically controlled regulating valve 9 are arranged to be operated by means of the control unit 13. The control unit 13 may be any suitable device, for example a unit shared by all the aforementioned elements, or each element may have its own control unit, etc.

FIG. 2 shows a modification of the example of FIG. 1. The example of FIG. 2 corresponds substantially to the example of FIG. 1. The only difference is that the arrangement of FIG. 2 comprises no air line. In FIG. 2, like reference numerals refer to like parts as in FIG. 1. The operation of the arrangement of FIG. 2 corresponds to the arrangement of FIG. 1. The only difference is that in the arrangement of FIG. 2 only anaesthetic gas, and no air, is mixed to the oxygen flow.

FIG. 3 shows a second embodiment of the arrangement according to the invention. In FIG. 3, like reference numerals refer to like parts as in FIG. 1. In this embodiment, an electronically controlled regulating valve 19 is placed in the anaesthetic gas line. The regulating valve 19 is preferably similar to the regulating valve 9 of FIG. 1. A mechanical flow control means 17 and a rotameter 17a are placed in a corresponding point in the air line. The on/off means of the air conduit, i.e. the valve 18, is normally open, which means that the valve must be electrically activated to close it. It opens automatically when the activation ends. The means 7 acts as a safety valve for the valve 19 also in this embodiment. By means of the valve 18, the supply of air is prevented when an anaesthetic gas has been chosen as the auxiliary gas.

The advantage of the arrangement of FIG. 3 is that the supply of air is independent of the supply of electrical energy. The disadvantage, as compared with the embodiment of FIG. 1, is the greater number of components for the mechanical control means 17 and the rotameter 17a. The rotameter has been placed in the air flow line for the approximate regulation of the flow. Otherwise the embodiment of FIG. 3 corresponds to the embodiment of FIG. 1.

FIG. 4 shows a third embodiment of the arrangement according to the invention. In FIG. 4, like reference numerals refer to like parts as in FIGS. 1 and 3. The example of FIG. 4 differs from the example of FIG. 3 in that in the example of FIG. 4, the valves 7 and 18 are replaced with an electronically controlled selector valve 20. The selector valve 20 is a valve provided with three gas connections and two flow conduits. When there is no electricity, the flow conduits run in such a way that air can flow freely through the valve and the anaesthetic gas is closed. When the electricity is switched on, the anaesthetic gas line opens, and the air line closes. The valve 20 also acts as a safety valve for the anaesthetic gas line so that the anaesthetic gas line closes when the valve is no longer activated. Otherwise, the example of FIG. 4 corresponds to the examples described above.

The advantage of the arrangement according to FIG. 4 over the arrangement of FIG. 3, for example, is that it requires only one selector valve instead of two closing valves. The disadvantage, on the other hand, is that the valve is larger and takes up more space.

The above-described embodiments are not intended in any way to restrict the invention, but the invention can be modified freely within the scope of the claims. Thus, it is clear that the arrangement according to the invention or its details do not necessarily have to be exactly like those described in the figures, but other kinds of arrangements are also possible.

We claim:

1. Apparatus for forming a breathing gas for a patient comprised of a mixture of oxygen and at least one other gas, said apparatus maintaining the oxygen content in the breathing gas at at least a desired minimum content, said apparatus comprising:

an oxygen supply conduit through which the oxygen flows;

a gas supply conduit means through which the other gas flows, said oxygen supply conduit and said gas supply conduit means being joined at a junction (11) from which the breathing gas mixture is discharged through an outlet conduit for supply to the patient;

mechanically operated flow regulating means in said oxygen supply conduit upstream of said junction, said means comprising a variable throttle valve means (4) for varying the flow rate of oxygen in said oxygen supply conduit through a range of flow rates and for establishing a given flow rate of oxygen in said oxygen supply conduit within said range to flow a desired quantity of oxygen per unit time through said oxygen supply conduit;

first flow measuring means (6) in said oxygen supply conduit upstream of said junction for ascertaining the amount of oxygen flowing said oxygen supply conduit and for providing an output in accordance therewith;

second flow measuring means (10) for ascertaining a gas flow amount in one of said gas supply conduit means and said outlet conduit and for providing an output in accordance therewith;

electrically operated flow regulating means (9) in said gas supply conduit means upstream of said junction for regulating the flow rate of the other gas flowing in said gas supply conduit means;

signal means (15) for providing a control signal indicative of the amount of other gas to be mixed with oxygen to form a breathing gas having not less than the desired minimum oxygen content; and an electronic control circuit (13) having inputs coupled to said first and second flow measuring means (6, 10) and to said signal means (15), said electronic control circuit having an output coupled to said electrically operabled flow regulating means (9), said electronic control circuit being responsive to the output of said signal means and the output of said first flow measuring means for determining a flow rate for the other gas flowing in said gas supply conduit means commensurate with the given flow rate of oxygen in said oxygen supply conduit established by said mechanically operable flow regulating means and that will establish at least the desired minimum oxygen content in the breathing gas, said electronic control circuit ascertaining differences between said determined flow rate of the other gas and the actual flow rate of the other gas provided by said second flow measuring means (10) and providing an output to said electrically operable flow regulating means (9) for altering the flow of the other gas in said gas supply conduit means to that which provides not less than the desired minimum oxygen content in the breathing gas discharged from said junction, said electronic control circuit operating said electrically operable flow regulating means (9) to vary the flow rate of the other gas as the given flow rate of oxygen is varied, thereby to maintain oxygen in the breathing gas at not less than the desired, minimum content as the given flow rate of oxygen is varied.

2. An apparatus according to claim 1 wherein said first flow measuring means (6) is further defined as located in said oxygen supply conduit downstream of said mechanical flow regulating means.

3. An apparatus according to claim 1 wherein said second flow measuring means (10) is further defined as located in said gas supply conduit means upstream of said junction (11) and downstream of said electrically operable flow regulating means (9).

4. An apparatus according to claim 1 further defined as forming a breathing gas comprised of a mixture of oxygen and another gas comprising nitrous oxide and wherein said gas supply conduit means is further defined as having nitrous oxide gas flowing therethrough.

5. An apparatus according to claim 1 further defined as forming a breathing gas comprised of a mixture of oxygen and at least on other gas comprising air and wherein said gas supply conduit means is further defined as having air flowing therethrough.

6. An apparatus according to claim 1 further defined as forming a breathing gas comprised of a mixture of oxygen, nitrous oxide, and air and wherein said gas supply conduit means is further defined as having nitrous oxide and air flowing therethrough.

7. An apparatus according to claim 1 further including an electrically operated on-off valve in said gas supply conduit circuit, said on-off valve being coupled to said electronic control circuit for being energized by said control circuit between flow blocking and flow permitting states, said on-off valve being placed in a given state when said on-off valve is deenergized.

8. An apparatus according to claim 3 further including an electrically operated on-off valve in said gas supply conduit means upstream of said second flow measuring means, said on-off valve being coupled to said electronic control circuit for being energized by said control circuit between flow blocking and flow permitting states, said on-off valve being placed in a given state when said on-off valve is deenergized.

9. An apparatus according to claim 4 further including an electrically operated on-off valve in said gas supply conduit means having nitrous oxide flowing therethrough, said on-off valve being coupled to said electronic control circuit for being energized by said control circuit between flow blocking and flow permitting states, said on-off valve being placed in the flow blocking state when said on-off valve is deenergized.

10. An apparatus according to claim 5 further including an electrically operated on-off valve in said gas supply conduit means having air flowing therethrough, said on-off valve being coupled to said electronic control circuit for being energized by said control circuit between flow blocking and flow permitting states, said on-off valve being placed in the flow permitting state when said on-off valve is deenergized.

11. An apparatus according to claim 6 wherein said gas supply conduit means comprises a nitrous oxide supply line and an air supply line, said nitrous oxide supply line and said air supply line being joined upstream of said junction to form said gas supply conduit means and wherein said nitrous oxide supply line and said air supply line each contain an electrically operated on-off valve coupled to said electronic control circuit for being energized by said control circuit between flow blocking and flow permitting states, the operation of said on-off valves selecting the gas or gases to be mixed with oxygen.

12. An apparatus according to claim 11 wherein said on-off valve in said nitrous oxide supply line is further defined as being placed in the flow blocking state when said on-off valve is deenergized and wherein said on-off valve in said air supply line is further defined as being placed in the flow permitting state when said flow controller is deenergized.

13. An apparatus according to claim 6 wherein said gas supply conduit means comprises a nitrous oxide supply line and an air supply line, said nitrous oxide supply line and said air supply line being joined upstream of said junction to form said gas supply conduit means, wherein said electrically controllable flow regulating means (19) is located in said nitrous oxide supply line, and wherein second mechanically operated flow regulating means is located in said air supply line, said second mechanical flow regulating means comprising a variable throttle means (17) for controlling the flow rate of air in said air supply line.

14. An apparatus according to claim 11 wherein said electrically operated flow regulating means (19) is located in said nitrous oxide supply line downstream of said electrically operated flow controller (7) in said nitrous oxide supply line, and wherein second mechanically operated flow regulating means is located in said air supply line, said second mechanically operated flow regulating means comprising a variable throttle means (17) for controlling the flow rate of air in said air supply line.

15. The apparatus according to claim 1 further including mechanical flow measuring means (5) in said oxygen supply conduit.

16. The apparatus according to claim 13 further including mechanical flow measuring means (17a) in said air supply conduit.

17. The apparatus according to claim 1 wherein said oxygen supply conduit and gas supply conduit means include pressure regulators for protecting the apparatus from pressure variations.

18. An apparatus according to claim 1 further defined as including anesthetic agent vaporization means coupled to said junction for receiving the breathing gas mixture discharged from said outlet conduit and for providing an anaesthesia agent to the breathing gas, said apparatus including further signal means coupled to said electronic control means for providing an output indicative of the amount of anaesthesia agent to be provided to the breathing gas, said control means being responsive to said output of said further signal means when determining the flow rate for the other gas.

* * * * *